United States Patent [19]

Franz et al.

[11] 3,941,854

[45] Mar. 2, 1976

[54] METHOD FOR PRODUCING STYRENE AND BENZENE

[75] Inventors: Raymond A. Franz, Baton Rouge, La.; Gary D. Madding, Evansville, Ind.; Tao P. Li, Chesterfield, Mo.

[73] Assignee: Monsanto Company, St. Louis, Mo.

[22] Filed: Apr. 25, 1974

[21] Appl. No.: 464,018

[52] U.S. Cl. .................... 260/669 R; 260/672 R
[51] Int. Cl.² .................... C07C 3/58; C07C 5/42
[58] Field of Search .................... 260/669 R, 672 R

[56] References Cited
UNITED STATES PATENTS

| | | | |
|---|---|---|---|
| 1,870,876 | 8/1932 | Smith et al. | 260/669 R |
| 3,374,280 | 3/1968 | Carr et al. | 260/672 R |
| 3,396,206 | 8/1968 | Scott | 260/669 R |
| 3,816,432 | 6/1974 | Franz | 260/669 R |

*Primary Examiner*—Paul M. Coughlan, Jr.
*Attorney, Agent, or Firm*—Elizabeth F. Sporar

[57] ABSTRACT

Styrene and benzene are simultaneously produced by heating a mixture of toluene and ethylbenzene in a mole ratio of at least 1:1 to a temperature from about 400° to 900°C at moderate pressures for a period of time up to about 15 seconds, cooling the reaction mixture quickly and recovering the styrene and benzene therefrom. Yields of both products can be improved by the addition of modifying agents such as benzenethiol or by conducting the reaction in the presence of a chromium-containing catalyst supported on an inorganic material which can be promoted by a compound of calcium, magnesium, copper or zinc.

10 Claims, No Drawings

METHOD FOR PRODUCING STYRENE AND BENZENE

BACKGROUND OF THE INVENTION

The present invention relates to a method for simultaneously producing styrene and benzene by reaction of toluene and ethylbenzene.

At the present time, styrene is made commercially by a multistep process starting with benzene which is alkylated with ethylene in the presence of a catalyst such as aluminum chloride to produce ethylbenzene which is then catalytically dehydrogenated to styrene. The dehydrogenation reaction is an endothermic one and its rate and the extent of conversion are limited by approach to thermodynamic equilibrium. The equilibrium limitation must be relieved in practice by low reaction pressures or by dilution with inert gases. It is well known that toluene can be dealkylated to benzene either thermally or catalytically by subjecting it in the presence of hydrogen to a temperature within the range from about 500° to about 1000°C at elevated pressure for a controlled period of time. As a result of such reaction conditions, the methyl group is cleaved from the toluene and replaced by hydrogen. The hydrodealkylation reaction is exothermic. It has now been discovered that these two reactions, the dehydrogenation of ethylbenzene and the hydrodealkylation of toluene, can be conducted either thermally or catalytically in the same reactor to provide a new method for producing styrene and benzene together utilizing less expensive reactants. The hydrogen and heat removal required in one reaction is provided by the other reaction taking place simultaneously. Energy requirements are reduced over the two separate processes, hydrodealkylation is effected at atmospheric or relatively low pressure, dehydrogenation is effected at atmospheric or higher pressure relative to those presently employed, no hydrogen recycle and clean-up is needed, hydrogen from the dehydrogenation of ethylbenzene reaction is effectively used without compression and capital costs are reduced as compared to requirements of two separate plants for separate production of styrene and benzene from ethylbenzene and toluene, respectively. It is especially remarkable that atmospheric pressure is successfully used in this dual reaction since the dealkylation of toluene alone requires at least 150 psi partial pressure of hydrogen to avoid aromatic condensation reactions leading to major yield losses to polynuclear aromatics. If desired, the ratio of benzene to styrene produced may be varied by modifications in process conditions.

STATEMENT OF THE INVENTION

According to the present invention, a mixture of toluene and ethylbenzene in a mole ratio of at least 1:1 is passed at moderate pressures through a reaction zone heated to a temperature from about 400° to about 900°C at a rate such that the reactants are exposed to said temperature for a period up to about 15 seconds, the resulting reaction effluent is quenched and styrene and benzene are recovered therefrom by conventional separation techniques. Improved results insofar as styrene and benzene yields are concerned are obtained if the reaction mixture contains a modifying agent such as benzenethiol and/or if the reactor walls and piping are sulfided by pumping a solution of a modifying agent such as benzenethiol in a suitable solvent such as cetane through the reactor for a few minutes prior to initial use. Even better results with respect to yields of styrene and benzene are obtained when a catalyst is employed comprising an oxide or salt of chromium or such chromium compounds promoted by an oxide or salt of a metal selected from Groups I and II of the Periodic Table supported on a low-surface-area material such as alumina.

DESCRIPTION OF THE PREFERRED EMBODIMENTS

The invention is illustrated in the following examples which, however, are not to be construed as limiting it in any particular manner.

EXAMPLE 1

In a series of runs, toluene (Tol) and ethylbenzene (EB) in a mole ratio of 4.2:1 were reacted thermally under one atmosphere pressure in a reactor comprised of a pair of ⅛ inch O.D. stainless steel preheater coils connected to a section of stainless steel tubing (½ inch O.D.) approximately 12. cm long. The free volume of the tube was 10.8 ml. The temperature of each preheater was set by manually selecting the voltage applied to the heater coil. The temperature of the reactor was controlled by a "Pyro-O-Vane" controller and a J-type thermocouple. The toluene and ethylbenzene were metered, mixed and fed to the pre-heater via glass syringes, the syringes being driven by hydraulic pistons. From the preheaters the feed was introduced without cooling into the reactor.

The effluent from the reactor was cooled by a water condenser and then by a series of three U-tubes cooled in a dry ice bath. The vent gas was sampled in small portions and most of the vent gas was recorded by a wet-test meter. After the run the condensates were combined and analylzed by gas chromatography. The gas sample was collected in an evacuated bulb and subjected to analysis using a mass spectrometer.

After each run the reactor was purged with steam and then any carbon deposit was burned out by purging the hot reactor with air for several hours. Variations in the conditions of the runs and the results obtained are presented in Table 1 below.

Table 1

| Run No. | Reaction Time Min. | Temp °C | Residence Time, sec | % Conversion of Tol | % Conversion of EB | % Yield SM* on EB | % Yield Bz on Tol |
|---|---|---|---|---|---|---|---|
| 1 | 60 | 720 | 5 | 14.4 | 83.1 | 41.7 | 40.6 |
| 2 | 60 | 700 | 5 | 11.3 | 52.3 | 69.3 | 43.9 |
| 3 | 30 | 700 | 10 | 32.4 | 70.5 | 51.2 | 20.7 |

*Styrene Monomer

EXAMPLE 2

Using essentially the same equipment, except that the stainless steel tubing was replaced by a coil having a diameter of 1-in. made from ½ inch O.D. stainless steel tubing (volume 13.7 ml), and following the procedure employed in Example 1, toluene and ethylbenzene were reacted over a reaction period of one hour at a temperature of 720°C and a residence time of 10 sec. in the presence of benzenethiol which was added to the charge to the reactor. In the first run, 400 ppm of benzenethiol was used, an amount sufficient only to sulfide the reactor, but in Run 2, the benzenethiol was increased to 1 mole per cent, a quantity such that it could act as a free-radical modifier. In addition, before starting these runs, the stainless steel reactor and preheaters were treated slowly with 5 ml benzenethiol in cetane and a warm-up of 10–20 minutes was made to bring the feed rates and reactor to equilibrium. Run conditions and results are presented in Table 2 below.

Table 2

| Run No. | Mole Ratio Tol/EB | % Conversion of EB | % Yield SM on EB | % Yield Bz on Tol |
|---|---|---|---|---|
| 1 | 14:1 | 91 | 58 | 70 |
| 2 | 14:1 | 89 | 65 | 79 |

The improvement in yields of both ethylbenzene and benzene is evident by comparison of these results with those shown in Example 1.

EXAMPLE 3

In this series of runs, toluene and ethylbenzene were reacted in contact with supported chromium-containing catalysts at atmospheric pressure. The apparatus employed consisted of a specially constructed jacketed Vycor reactor. The inner tube, 1 inch in diameter and 16 inches in length, had a frit fixed at a position about 3.5 inches above the bottom as a catalyst support. The outer jacket was about 3 inches in diameter and was filled with sand which was fluidized by nitrogen to maintain uniform temperature. The reactor was heated by a furnace. The reactor temperature was measured by a thermocouple connected to a temperature indicator and was controlled by another thermocouple placed in the same bath which was connected to a temperature control.

The feed materials, supplied either from a constant pressure feed tank or a syringe pump passed through a vaporizer and entered the top of the reactor. The effluent leaving the bottom of the reactor was cooled by two ice-water condensers from which liquid products were collected. The uncondensed gases were analyzed by a gas chromatograph sampling directly from the gas line.

The gas flow rate was measured frequently by a bubble meter. The reactor was also equipped with rotameters, flow regulators and pressure controllers for hydrogen, nitrogen and air. These gases were used either as feed diluents or as catalyst treating agents.

The various catalysts employed were prepared by an impregnation technique wherein the support was mixed with a water solution of the desired catalytic metal compound in an amount that could be completely absorbed by the support. The impregnated solid was dried with an infrared heater and then in an oven at 110°C overnight. The dry solid was calcined at temperatures from 500° to 600°C for three to eight hours depending upon the composition of the catalyst and the metal salts used. The catalyst in Run 1 was prepared by an ion exchange method wherein chromium chloride ($CrCl_3 \cdot 6H_2O$) was dissolved in water to make a 0.5 molar solution. This solution was mixed with an air-dried, sodium-form zeolite to allow the exchange of the metal cation and the sodium ion. About three times equivalent excess of the cation was used. The exchange was conducted at ambient temperature for 96 hours. The zeolite was filtered and washed with distilled water until free from the anion. It was dried at 110°C overnight and then treated with hydrogen at 600°C for three hours.

From about 25 to about 50 ml. of the catalyst were placed in the reactor and the feed mixture was passed through the catalyst bed at a predetermined temperature and flow rate. The feed mixture was vaporized and preheated to about 150°C in a vaporizer before entering the top of the reactor. Hydrogen was introduced with the reactants to prevent coke formation in the reactor. The reactor effluent, after condensing liquid product, was measured and sampled for gas chromatographic analysis. A period of 30 to 45 minutes was allowed to equilibrate the whole system before collection of the liquid and gas samples. Generally, from 30 minutes to an hour was sufficient to collect a representative liquid sample. The catalysts employed, the conditions under which they were used and the results obtained are presented in Table 3. Comparison of the data presented with those of the previous examples shows that yields of both styrene and benzene are significantly increased when a chromium-containing catalyst is employed in the reaction and that the effectiveness of the chromium-containing catalyst can be further enhanced by addition thereto of a Group I or Group II metal compound.

TABLE 3

| Run No. | Mole Ratio Tol/EB | Catalyst Composition | Promoter - Amt % | Temp °C | Residence Time Sec. | Mole Ratio $H_2$/HC | Conversion, % Tol[1] | Conversion, % EB | % Yield SM on EB | % Yield Bz on Tol |
|---|---|---|---|---|---|---|---|---|---|---|
| 1 | 4:1 | 5% Cr on Zeolon Na[2] | None | 600 | 2.5 | 0 | 5.0 | 18.5 | 94.9 | 100 |
| 2 | 4:1 | 5% Cr on $Al_2O_3$ | None | 600 | 2.5 | 1 | 36.3 | 18.6 | 100 | 100 |
| 3 | 4:1 | 5% Cr on $Al_2O_3$ | None | 650 | 2.5 | 1 | 20.0 | 44.9 | 93 | 100 |
| 4 | 4:1 | 2.5% Cr on $Al_2O_3$ | None | 600 | 13.4 | 2 | 30.9 | 34.7 | 76.4 | 100 |
| 5 | 4:1 | " | Zn 3.14 | 600 | 13.4 | 2 | 75.8 | 29.8 | 79.2 | 100 |
| 6 | 4:1 | " | Cu 3.05 | 600 | 13.4 | 2 | 42.2 | 28.7 | 96.0 | 100 |
| 7 | 4:1 | " | Mg 1.17 | 600 | 13.4 | 2 | 60.4 | 20.0 | 100 | 100 |
| 8 | 4:1 | " | Ca 1.93 | 600 | 13.4 | 2 | 42.8 | 22.9 | 100 | 100 |
| 9 | 4:1 | 5% Cr on $Al_2O_3$ | None | 625 | 1.67 | 2 | 3.9 | 25.4 | 95.3 | 100 |
| 10 | 4:1 | " | Zn 2 | 625 | 1.67 | 2 | 30.4 | 36.9 | 85.4 | 100 |
| 11 | 4:1 | " | Cu 2 | 625 | 1.67 | 2 | 13.0 | 36.6 | 77.8 | 100 |

[1] % of Theoretical = $\frac{\text{Moles Bz from Tol}}{\text{Moles SM Produced}} \times 100$

[2] Catalyst prepared by ion exchange as described above. All others prepared by impregnation.

EXAMPLE 4

Catalysts comprising 2.5% chromium and 1.17% magnesium were prepared as described in Example 3 on several supports having different surface areas. The catalysts were then employed in reacting toluene and ethylbenzene as described in Example 3 using a Tol/EB ratio of 4, a temperature of 600°C, a contact time of 13.4 seconds and a $H_2$/HC ratio of 2. Results presented in Table 4 below show that the most suitable supports are those having a low surface area since they produce high conversion of toluene and high selectively to styrene.

Table 4

| Run No. | Support | Surface Area $m^2/g$ | Conversion, % Tol[1] | Conversion, % EB | % Yield SM on EB | % Yield Bz on Tol |
|---|---|---|---|---|---|---|
| 1 | Alumina | 9 | 60.4 | 20 | 100 | 100 |
| 2 | '' | 0.05 | 74.1 | 15.6 | 97.7 | 100 |
| 3 | '' | 0.5 | 82.3 | 15.0 | 100 | 100 |
| 4 | '' | 15 | 34.8 | 28.8 | 86.2 | 100 |
| 5[2] | '' | 33 | 8.9 | 29.9 | 85.9 | 100 |
| 6 | Silica | 0.5 | 49.3 | 20.8 | 98.5 | 100 |
| 7 | Celite | 2.4 | 44.3 | 27.0 | 82.2 | 100 |

[1]% of Theoretical = $\frac{\text{Moles Bz from Tol}}{\text{Moles SM Produced}} \times 100$

[2]Contact time 6.68 sec.

Many variations in conditions from those given in the examples can be made without departing from the invention. Thus, the temperature may vary from 400° to 900°C depending upon whether a catalyst is employed or not. With chromium-containing catalysts, temperatures from 500°–700°C are generally suitable with a temperature from about 600°–650°C being preferred. The reaction conducted thermally or with a modifying agent such as benzenethiol requires a temperature from about 600° to about 900°C with temperatures in the range from about 625° to about 825°C being preferred.

One of the advantages of the process of the invention is that it can be carried out at atmospheric pressure or at relatively low pressures, i.e., up to about 100 psia, although higher or lower pressures can be employed if desired.

The mole ratio of toluene to ethylbenzene is preferably maintained in the range from 2:1 to 8:1 to maintain parallel hydrodealkylation and dehydrogenation and yet avoid excessive recycling of toluene. Preferably, the Tol/EB mole ratio is about 4:1. However, mole ratios of toluene to ethylbenzene in the range from about 1:1 to about 15:1 can be employed.

Residence time in the reactor can likewise be varied from about 1 to about 15 seconds. Preferably, a residence time of 2 to 10 seconds is used in the thermal reaction and from about 2 to about 8 seconds in the catalyzed reaction.

Modifying agents which function to improve conversion of ethylbenzene in the thermal reaction are well known and can be selected from the group consisting of (1) $H_2S$, HBr, HCl, HI and combinations thereof and (2) compounds and elements which under the conditions in the reaction zone will form $H_2S$, HBr, HCl, HI and combinations thereof. A comprehensive description and listing of such agents, in addition to the preferred agent, benzenethiol exemplified herein, is disclosed in U.S. Pat. No. 3,449,457 which is incorporated herein by reference.

The amount of modifying agent necessary in carrying out the process is that which causes a molar concentration in the reaction mixture of not less than 0.01 mole per cent of $H_2S$, HBr, HCl, HI or combinations thereof. Amounts up to as high as 25 mole per cent of the modifying agent in the reaction mixture can be employed. However, the preferred amount is that which will produce a concentration of $H_2S$, HBr, HCl, HI or combinations thereof in admixture with the hydrocarbon reactant mixture in the range from about 0.5 to about 5.0 mole per cent.

The catalysts useful in the invention are those containing chromium in an amount up to about 10% supported on an inorganic carrier material. Suitable support materials are, for example, alumina, silica, alumina-silica mixtures, activated charcoal, diatomaceous earth and the like. Low surface area materials, i.e., those which have a surface area of less than 15 $m^2/g$ are preferred since they result in high conversion of toluene and high selectivity to styrene as shown in Example 4. The higher surface area materials give increased conversions of ethylbenzene but low toluene conversion and low styrene selectivity.

Improved conversion of toluene can be obtained when a promoter chosen from the compounds of the metals of Groups I-B, II-A and II-B is also employed with the chromium-containing metal catalyst. Preferred among these compounds are copper, magnesium, calcium and zinc with magnesium compounds being especially preferred. The amount of promoter compound to be employed is generally that required to provide an atomic ratio of chromium to promoter metal between 0.5 and 2. With the preferred promoter metal, magnesium, an atomic ratio of 1 is preferred. The conversion of ethylbenzene and toluene and the styrene selectivity with the chromium-magnesium catalyst depend upon the concentration of the metals and the ratio of chromium to magnesium. An increase in the metal content from 0.1 g-atom per 100 g of support to 0.2 g-atom per 100 g of support improves ethylbenzene conversion but lowers toluene conversion. Best reaction performance is achieved at a 1:1 chromium to magnesium ratio at a metal content of 0.1 g-atom per 100 g of support. An excess of either component results in lower toluene conversion and lower styrene selectivity approaching that of unpromoted catalysts.

The catalysts are readily prepared by techniques well known in the art. The usual method involves dissolving a compound of the metal or metals such as a halide, nitrate, oxide, acetate, etc., in a suitable solvent such as water to provide a solution of the desired concentration, impregnating the support with the solution, drying and calcining the dry solid at temperatures from 500° to 600°C for about 3 to about 8 hours.

The reactor may be of any suitable design. To avoid the necessity of heating large masses of reactor material, it is desirably of tubular shape. Appropriate materials of construction include ceramic-lined steel and nickel-chromium alloys and also quartz-lined reactors. To maintain the reactor free from coke, diluent hydrogen can be fed with the reactants in amounts depending upon the toluene conversion and the degree of coke suppression desired. Generally, an amount from about 1 – 2 moles of hydrogen per mole of hydrocarbon is employed. The reaction effluentt is usually cooled quickly to limit side reactions and to preserve the styrene against further reactions such as decomposition and polymerization and thus improve the yield. Cooling is effected by conventional heat exchange equipment, by introducing a cool inert gas such as helium, nitrogen, water-vapor and the like into the hot reaction mixture, or by injection of a compatible liquid such as toluene. The products of the reaction are then separated by conventional techniques of flashing, absorption and fractional distillation.

What is claimed is:

1. A process for the simultaneous dehydrogenation of ethylbenzene and the hydrodealkylation of toluene which comprises passing a mixture consisting essentially of toluene and ethylbenzene in mole proportions from about 1:1 to about 15:1 through a reaction zone maintained at a pressure up to about 100 psia and heated to a temperature from about 400° to about 900°C at a rate such that the reactants are exposed to said temperature for a period up to about 15 seconds, quenching the reaction effluent and recovering the styrene and benzene therefrom.

2. The process of claim 1 wherein a modifying agent is employed which is selected from the group consisting of (1) $H_2S$, HBr, HCl, HI and combinations thereof and (2) compounds and elements which under the conditions in the reaction zone will form $H_2S$, HBr, HCl, HI and combinations thereof.

3. The process of claim 2 wherein said modifying agent is benzenethiol.

4. The process of claim 3 wherein said temperature is from about 600° to about 900°C.

5. The process of claim 1 wherein said toluene and said ethylbenzene are contacted in said reaction zone with a catalyst comprising a compound of chromium supported on an inorganic material.

6. The process of claim 5 wherein said reaction temperature is in the range from about 500° to about 700°C.

7. The process of claim 6 wherein said inorganic material is alumina.

8. The process of claim 7 wherein said catalyst contains in addition to said chromium compound, a promoter chosen from the group consisting of the compounds of calcium, magnesium, copper and zinc.

9. The process of claim 8 wherein said promoter is a compound of magnesium.

10. The process of claim 9 wherein the atomic ratio of chromium to magnesium in said catalyst is between 0.5 and 2.0.

* * * * *